(12) United States Patent
Ibanez Ballesteros et al.

(10) Patent No.: US 11,486,823 B2
(45) Date of Patent: Nov. 1, 2022

(54) INTERCHANGEABLE SENSOR DEVICE FOR A FUNCTIONAL NEAR-INFRARED SPECTROSCOPY SYSTEM

(71) Applicants: UNIVERSIDAD MIGUEL HERNANDEZ, Alicante (ES); CONSEJO SUPERIOR DE INVESTIGACIONES CIENTIFICAS, Madrid (ES)

(72) Inventors: Joaquin Ibanez Ballesteros, Alicante (ES); Carlos Belmonte Martinez, Alicante (ES)

(73) Assignees: UNIVERSIDAD MIGUEL HERNANDEZ, Elche Alicante (ES); CONSEJO SUPERIOR DE INVESTIGACIONES CIENTIFICAS, Madrid (ES)

( * ) Notice: Subject to any disclaimer, the term of this patent is extended or adjusted under 35 U.S.C. 154(b) by 865 days.

(21) Appl. No.: 16/305,722

(22) PCT Filed: May 24, 2017

(86) PCT No.: PCT/ES2017/070348
§ 371 (c)(1),
(2) Date: Dec. 3, 2019

(87) PCT Pub. No.: WO2017/207841
PCT Pub. Date: Dec. 7, 2017

(65) Prior Publication Data
US 2020/0378889 A1  Dec. 3, 2020

(30) Foreign Application Priority Data

May 30, 2016 (ES) .............................. ES201630689U

(51) Int. Cl.
*G01N 21/359* (2014.01)
*A61B 5/00* (2006.01)
*A61B 5/026* (2006.01)

(52) U.S. Cl.
CPC .......... *G01N 21/359* (2013.01); *A61B 5/0075* (2013.01); *A61B 5/0261* (2013.01)

(58) Field of Classification Search
CPC .. G01N 21/359; A61B 5/0075; A61B 5/0261; A61B 5/0064; A61B 5/14546; A61B 5/14553; A61B 5/14552
See application file for complete search history.

(56) References Cited

U.S. PATENT DOCUMENTS

2015/0038812 A1\* 2/2015 Ayaz .................... A61B 5/6814
600/328
2016/0022223 A1  1/2016 Grundfest et al.
(Continued)

OTHER PUBLICATIONS

James Dieffenderfer, "Towards a Smart Bandage with Functional Near Infrared Spectroscopy Capability"; Paper; 2013; 13-15; IEEE Topical Conference on Biomedical Wireless Technologies, Networks, and Sensing Systems.

*Primary Examiner* — Allen Porter
*Assistant Examiner* — Abid A Mustansir
(74) *Attorney, Agent, or Firm* — Hayes Soloway PC

(57) ABSTRACT

An interchangeable sensor device for a functional near-infrared spectroscopy system (fNIRS) is a non-invasive device intended to detect changes in the concentration of hemoglobin species on any body surface area. The device includes a plurality of measurement units having different elastic configurations, each intended to be adapted to a specific area of the body, and a control unit for controlling any of the measurement units. Each of the measurement units is equipped with a first connector and the control unit is equipped with a second connector, which connectors
(Continued)

allow the control unit to be interchangeably connected to any of the measurement units.

11 Claims, 2 Drawing Sheets

(56) References Cited

U.S. PATENT DOCUMENTS

2016/0262674 A1* 9/2016 Esenaliev .......... A61B 5/14546
2016/0338630 A1* 11/2016 Matsui ................ A61B 5/6803
2018/0220968 A1* 8/2018 Funane .............. A61B 5/14553

* cited by examiner

US 11,486,823 B2

INTERCHANGEABLE SENSOR DEVICE FOR A FUNCTIONAL NEAR-INFRARED SPECTROSCOPY SYSTEM

CROSS-REFERENCE TO RELATED APPLICATIONS AND PRIORITY

This patent application claims priority from PCT/ES2017/070348 filed May 24, 2017, which claims priority from ES U201630689 filed May 30, 2016. Each of these patent applications which are herein incorporated by reference in their entirety.

OBJECT OF THE INVENTION

The object of the present invention is a non-invasive interchangeable sensing device for a functional near infrared (fNIR) spectroscopy system intended to detect changes in the concentration of haemoglobin species on any body surface.
Preferably, this body surface is a brain surface.

BACKGROUND OF THE INVENTION

Neurophysiological and neuroimaging technologies have contributed in recent years to the study of brain functioning.
The most common modalities of functional neuroimaging techniques are functional magnetic resonance imaging (fMRI), positron emission tomography (PET), both based on the indirect image of hemodynamic changes resulting from neuronal activity.
On the other hand, magneto-encephalography (MEG) and electroencephalography (EEG) techniques, which are direct imaging technologies based on the electric-magnetic manifestations of neuronal activity, are also known.
Currently, these techniques have limitations in terms of explaining the neuronal bases of biological processes since MEG and EEG technologies have a high temporal resolution but a low spatial resolution, while the opposite happens with fMRI and PET technologies.
Because of this, functional near infrared (fNIR) spectroscopy has recently begun to be used. FNIR spectroscopy is an emerging technology that uses near-infrared light to measure changes in the concentration of oxygenated haemoglobin (HbO) and deoxygenated haemoglobin (Hb) in different parts of the body including the cerebral cortex. FNIR spectroscopy has a temporal resolution of the order of seconds and a spatial resolution in the order of centimetres. Among other advantages it also stands out for being a noninvasive technique, safe for the user and cheap.
Despite this, various problems have been encountered in using this fNIR technology in different parts of the body. These problems are mainly due to the fact that the morphological configuration of the measurement sensor does not adequately adapt to the surface of the human, allowing the passage of ambient light and introducing unwanted light signals that produce errors in the measurements.
In addition, the current systems using this fNIR technology are poorly portable systems due to their large volume and are very limited to a specific application for a typical user, as their measurement sensors are not adaptable to different parts of the body, or to different morphologies of the same part of the body that different users may have. This is mainly because each part of the body has a different shape that can vary with the age and morphology of the user.

DESCRIPTION OF THE INVENTION

The present invention describes an interchangeable sensing device for a functional near infrared (fNIR) spectroscopy system to detect changes in the concentration of haemoglobin species on a body surface.
Preferably, this surface is a cranial surface for the fNIR system to detect changes in the concentration of haemoglobin species on the surface of the frontal cerebral cortex.
The interchangeable sensor device comprises:
  a plurality of units of measurement with different elastic configurations each designed to adapt to a body surface, where each unit of measurement comprises a first connector; and
  a control unit intended to control any of the units of measurement, wherein the control unit comprises a second connector which is connected to the first connector.
All units of measurement comprise:
  an elastic base comprising transmitting and receiving compartments with light guides,
  a plurality of transmitters, located in transmitting compartments, intended to emit a first luminous signal on the body surface,
  a plurality of receivers, located in the receiving compartments, intended to receive a second luminous signal from the body surface through the light guides,
  a measuring base plate, linked to the plurality of transmitters and receivers, comprising the first connector,
  a receptacle intended to protect the transmitters, receivers and the measuring base plate comprising a hole allowing the first connector to pass through, and
  a first clamping strap which at least covers the plurality of transmitters and receivers and which is intended to be linked to at least a first clamping mechanism to adjust the interchangeable sensing device to the body surface, and/or
  a second clamping strap comprising a hole allowing the passage of the first connector, wherein the second strap wraps around the receptacle and is intended to be linked to at least a second clamping mechanism for adjusting the interchangeable sensing device to the body surface.
More specifically, each unit of measurement comprises different configurations to adapt to the surface of different body areas, although preferably cranial areas.
Preferably, the unit of measure comprises at least two receivers per transmitter.
It should be noted that both the first and second fastening mechanism preferably use an elastic band that can be adapted to the user's body and can adjust the surface of the elastic base to the body surface in order to prevent ambient light from entering and creating interference in the transmitters or receivers.
The connection between the clamping straps and the fastening mechanisms is preferably made by means of a clip system, a Velcro system, a sewing system or a combination of the above.
As for the control unit, it comprises a rigid receptacle which houses:
  a control base plate comprising the second connector to be linked to the unit of measurement in order to manage the first and second signals,
  a data transfer unit to transfer the second signal to an external computer unit which, using this second signal, calculates and detects changes in the concentration of haemoglobin species on the brain surface,
  an interface for transmitting luminous and/or acoustic signals on the operating status of an interchangeable sensor device, a power supply unit for powering both base plates, transmitters, receivers, the data transfer unit and the interface, and wherein this control base plate is intended to control the transmitters and receivers of the unit of measurement, as well as the data transfer unit and the interface.

More specifically, the data transfer unit comprises a wireless and/or wired transfer mechanism intended to establish communication with the external computer unit.

Preferably, the data transfer unit is a WiFi or Bluetooth receiver/transmitter.

Preferably, the data transfer unit is a USB port.

This results in an interchangeable sensor device that allows units of measurement from different configurations to be used by simply disconnecting the unit of measurement and connecting another unit with a different configuration. For example, these units of measurement may have different distances between transmitters and receivers, or increase or decrease the number of these, have different ways to adapt different parts of the skull and even an individual's body. In addition, it is also possible to have several control units whose control base plate is configured for different, special electronic control situations, allowing these to be combined with any of the measurement units.

DESCRIPTION OF THE DRAWINGS

To supplement the description being given and with the aim of promoting a better understanding of the characteristics of the invention, in accordance with a preferred example of a practical embodiment of the same, a set of drawings are provided as an integral part of the description in which, for merely illustrative purposes, the following has been represented.

PREFERRED EMBODIMENT OF THE INVENTION

Figure 1:
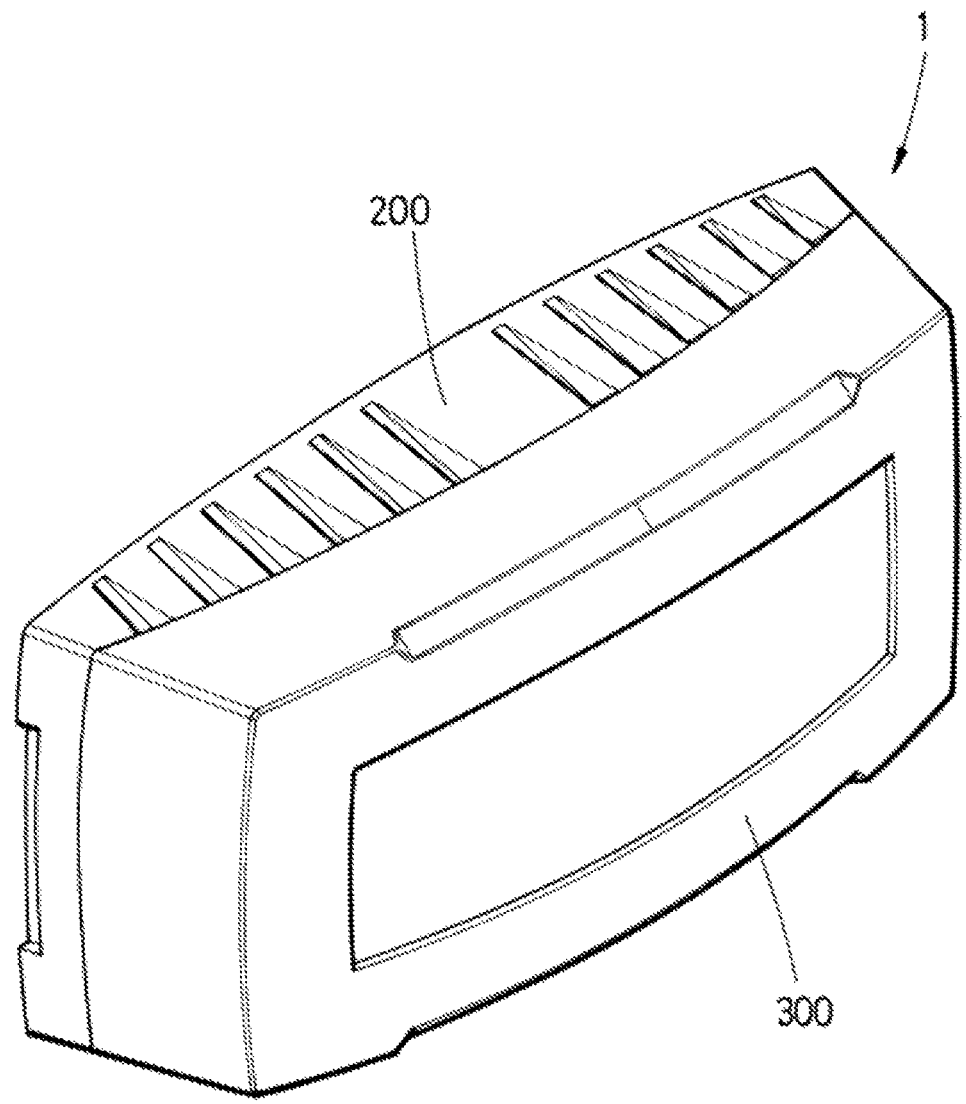
FIG. 1. Shows a schematic view of a preferred embodiment of the interchangeable sensor device FIG. 2. Shows an expanded schematic view of the preferred embodiment of the interchangeable sensor device

In a preferred embodiment, as shown in FIG. 1, the present invention describes an interchangeable sensor device (1) comprising:
  a unit of measurement (200) with an elastic configuration intended to be fitted to the forehead of an individual, and comprising a first connector (212); and
a control unit (300) intended to control the unit of measurement (200), and comprising a second connector (312) to connect to the first connector (212).

Figure 2:
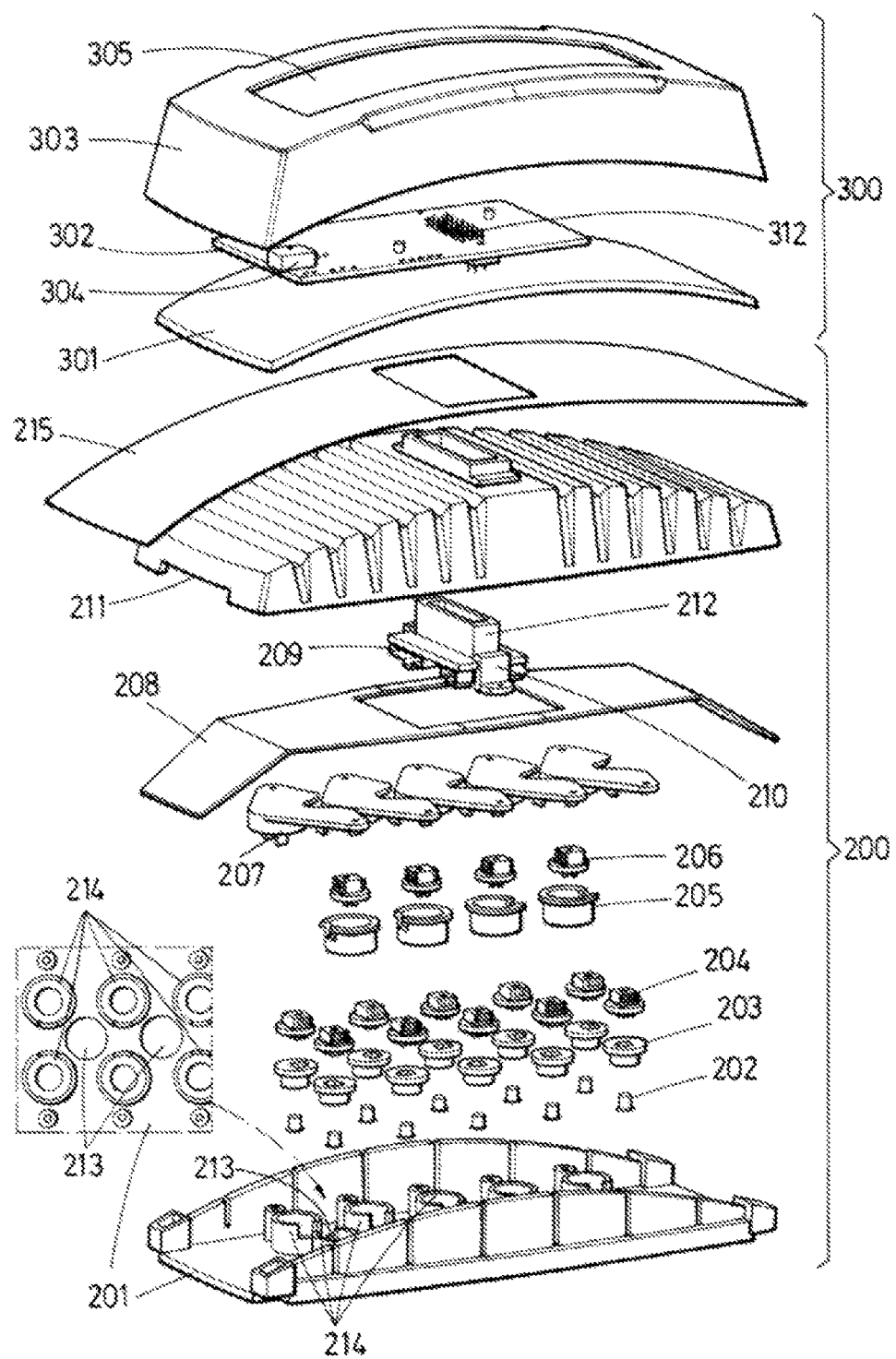

More specifically, as FIG. 2 shows, the unit of measure (200) comprises:
  an elastic base (201) with four transmitting compartments (213) and ten receiving compartments (214) with ten light guides (202),
  four transmitters (206), intended to emit a first luminous signal on the forehead surface, and which are located in four transmitting compartments (213) by means of four first adapters (205),
  ten receivers (204), intended to receive a second luminous signal from the surface of the forehead and through the light guides (202), and which are located in ten receiving compartments (214) by means of four second adapters (203),
  a pressure cap (207) comprising a flat body of 5 adaptable modules covering the transmitters (206) and receivers (204) to ensure that they do not move from their adapters (205, 203), and to protect them from impacts,
  a first clamping strap (208) covering that pressure cap (207) and comprising a hole, wherein that first clamping strap (208) is intended to be linked to clamping mechanisms for adjusting the interchangeable sensing device (1) to the individual's skull,
  a measuring base plate (209) with electronic circuitry linked to the transmitters (206) and receivers (204) by wiring through the hole of the first clamping strap (208); this measuring base plate (209) comprising the first connector (212), and linked to the elastic base (201) by means of two clip fastening mechanisms (210),
  a receptacle (211) resting on the elastic base (201) and comprising a hole intended to receive the first connector (212), in such a way that the receptacle (211) protects the transmitters (206) and receivers (204) from ambient light, and
  a second clamping strap (215) comprising a hole allowing the passage of the first connector (212), wherein the second strap (215) surrounds the receptacle (211) and is intended to be linked to at least a second clamping mechanism for adjusting the elastic base (201) to the cranial surface.

In addition, each emitter (206) comprises a first LED diode that emits a wavelength signal in the near infrared, preferably 740 nm, and a second LED diode that emits a wavelength signal in the near infrared, preferably 860 nm. Just as each receiver (204) comprises a photodetector to receive a wavelength signal in the near infrared, this wavelength is preferably between 690 and 900 nm.

Preferably, the four transmitters (206) are arranged in one line and surrounded by a first line of five of the ten receivers (204), and by a second line of five of the ten receivers (204) in such a way that each transmitter (206) is surrounded by four receivers (204).

As for the control unit (300), this comprises a rigid receptacle (303) which houses:
  a contact plate (301) comprising a hole,
  control base (302) comprising the second connector (312) that passes through the hole in the contact plate (301) to link up with the unit of measurement (200) used to manage the first and second signals,
  a data transfer unit (304) integrated in the base plate (302), to transfer the second signal to an external computer unit to use this second signal to calculate and detect changes in the concentration of haemoglobin species on the brain surface,
  an interface (305) to emit luminous and/or acoustic signals on the operating status of the interchangeable sensor device (1),
  a power supply unit, not represented, to supply both base plates (209, 302), the transmitters (206), the receivers (204), the data transfer unit (304) and the interface (305), and
  wherein this control base plate (302) is intended to control the transmitters (206) and receivers (204) of the unit of measurement (200), as well as the data transfer unit (304) and the interface (305).

It should be noted that HbO absorbs infrared radiation more intensely at these wavelengths than Hb and vice versa, thus the second signals comprise this information and through the external computer unit it is possible to measure the relative variations in concentration of both species of haemoglobin through the equations derived from the Lambert-Beer law.

The invention claimed is:

1. Interchangeable sensor device for a near-infrared functional (fNIR) spectroscopy system intended to detect changes in the concentration of haemoglobin species on a body surface; wherein such interchangeable sensor device comprises:
- an elastic base comprising a plurality of transmitting compartments and a plurality of receiving compartments:
- a plurality of transmitters positioned in the transmitting compartments, isolating each of the transmitters, wherein the transmitters are positioned to emit a first luminous signal on the body surface,
- a plurality of receivers positioned in the receiving compartments, isolating each of the receivers, wherein the receivers are positioned to receive a second luminous signal from the body surface,
- light guides located in the receiving compartments, separable from the receivers, through which the receivers receive the second luminous signal, and
- a measuring base plate electrically linked to the transmitters and receivers, comprising a first connector,
- a control unit intended to control the transmitters and the receivers, and wherein the control unit comprises a second connector engageable with the first connector.

2. The interchangeable sensor device, according to claim 1 further comprising:
- a receptacle to protect and encapsulate the transmitters, receivers and the measuring base plate,
- a first clamping strap which at least covers the transmitters and receivers and which is intended to be linked with at least a first clamping mechanism to adjust the interchangeable sensing device to the body surface, and/or
- a second clamping strap comprising a hole allowing the passage of the first connector, wherein the second clamping strap surrounds the receptacle and is intended to be linked to at least a second clamping mechanism for adjusting the interchangeable sensing device to the body surface.

3. The interchangeable sensor device according to claim 1 wherein each transmitter comprises a first LED diode and a second LED diode configured to emit a wavelength signal in the near infrared respectively.

4. The interchangeable sensor device according to claim 3 wherein the first LED diode is configured to emit a wavelength signal of 740 nm and the second LED diode is configured to emit a wavelength signal of 860 nm.

5. The interchangeable sensor device according to claim 1, wherein each receiver comprises at least one photodetector to receive at least one near-infrared wavelength signal from the cranial surface.

6. The interchangeable sensor device according to claim 5, wherein the wavelength is between 690 and 900 nm.

7. The interchangeable sensor device according to claim 1, wherein the plurality of transmitters and the plurality of receivers further comprise at least two receivers for each transmitter.

8. The interchangeable sensor device according to claim 1, wherein the control unit comprises:
- a control base plate comprising the second connector linked to and in communication with the transmitters and the receivers to manage the first and second signals,
- a data transfer built into the base plate in communication with an external computer, whereby the data transfer unit communicates the second signal to the external computer to calculate and detect changes in the concentration of haemoglobin species on the brain surface,
- an interface to emit luminous and/or acoustic signals on the operating status of an interchangeable sensor device,
- a power supply unit electrically connected to power both of the base plates, the transmitters, the receivers, the data transfer unit and the interface, and a rigid receptacle of a material of greater rigidity that the rest of the interchangeable sensor device which houses the control base plate, the data transfer unit, the interface, and the power supply unit,
- wherein the control base plate controls the transmitters and receivers, the data transfer unit and the interface.

9. The interchangeable sensor device according to claim 8, wherein the data transfer unit comprises a wireless and/or wired transfer mechanism intended to establish a communication with the external computer unit.

10. The interchangeable sensor device according to claim 8, wherein the data transfer unit is a WiFi or Bluetooth receiver/transmitter.

11. The interchangeable sensor device according to claim 8, wherein the data transfer unit is a USB port.

* * * * *